United States Patent [19]

Owens et al.

[11] 4,038,705

[45] Aug. 2, 1977

[54] ROTATIONAL JOINT ASSEMBLY FOR THE PROSTHETIC LEG

[75] Inventors: Lester J. Owens, Titusville; William C. Jones, Merritt Island, both of Fla.

[73] Assignee: The United States of America as represented by the Administrator of the National Aeronautics and Space Administration, Washington, D.C.

[21] Appl. No.: 710,032

[22] Filed: July 30, 1976

[51] Int. Cl.² .......................... A61F 1/08; A61F 1/04
[52] U.S. Cl. .................................................. 3/2; 3/21
[58] Field of Search .................. 3/2, 7, 21, 30–35

[56] References Cited

U.S. PATENT DOCUMENTS

| | | | |
|---|---|---|---|
| 3,731,323 | 5/1973 | Glancy | 3/2 |
| 3,842,443 | 10/1974 | Weber | 3/2 |
| 3,906,552 | 9/1975 | Weber | 3/2 X |
| 3,956,775 | 5/1976 | Moore | 3/2 |

Primary Examiner—Ronald L. Frinks
Attorney, Agent, or Firm—James O. Harrell; John R. Manning

[57] ABSTRACT

A rotational joint assembly for a prosthetic leg which enables an artificial foot to rotate slightly when a person is walking, running or turning. The prosthetic leg includes upper and lower tubular members with the rotational joint assembly interposed therebetween. The rotational joint assembly includes a restrainer mechanism which consists of a pivotably mounted paddle element engaging a resilient device for applying a limiting force to control the rotation of the foot and also restoring torque to return the foot back to its initial position.

3 Claims, 4 Drawing Figures

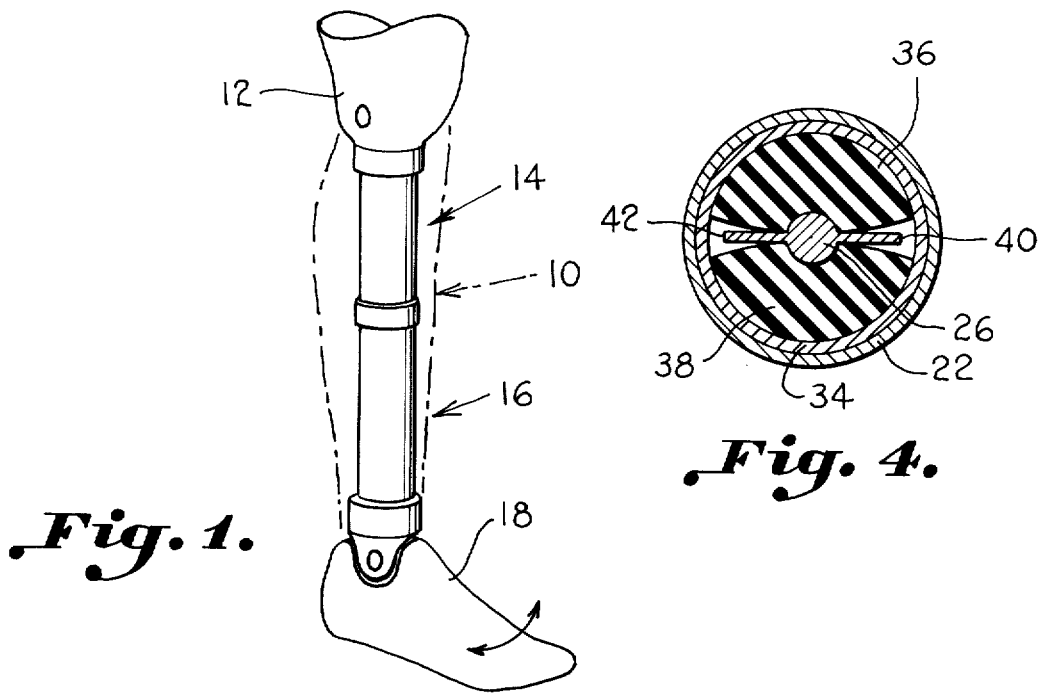
Fig. 1.
Fig. 4.
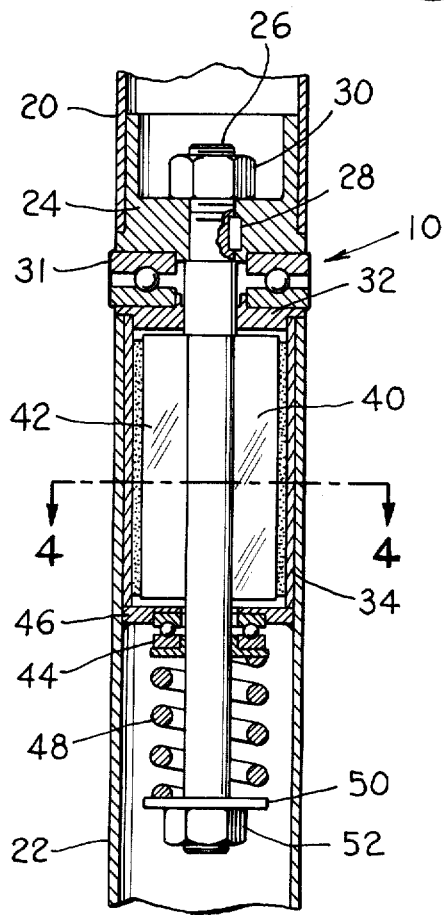
Fig. 2.
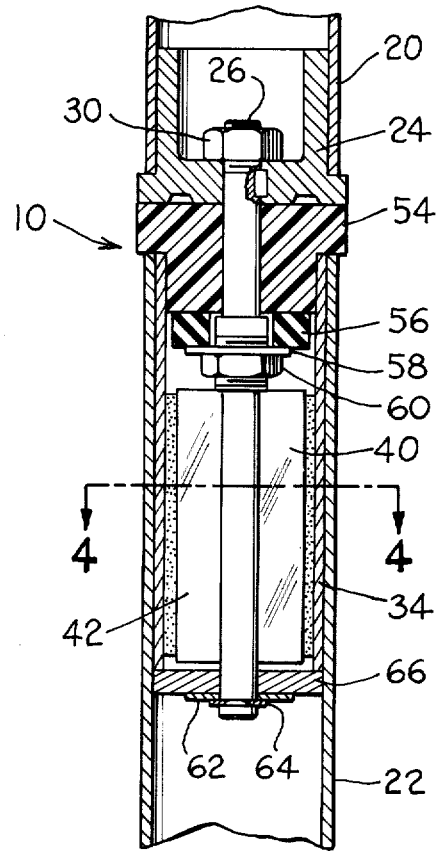
Fig. 3.

ROTATIONAL JOINT ASSEMBLY FOR THE PROSTHETIC LEG

ORIGIN OF THE INVENTION

The invention described herein was made by employees of the United States Government and may be manufactured by or for the Government for governmental purposes without the payment of any royalites thereon or therefor.

BACKGROUND OF THE INVENTION

The present invention relates to a rotational joint assembly for a prosthetic leg and more particularly to a restrainer mechanism which applies a restraining force for limiting the rotation of an artificial foot during walking and for applying a restoring torque thereto.

In the normal function of the human leg during walking, there is a rotation of the foot in relation to the hips. Lack of this rotational capability in a prosthetic leg results in an awkward gait requiring excessive efforts during walking and thereby producing an uneven wear of shoes.

An example of a joint for allowing rotation of an artificial foot is disclosed in U.S. Pat. No. 3,842,443 granted on Oct. 22, 1974. In this particular device, joint segments are attached to respective sections of a prosthetic leg. A resilient sleeve is arranged about the joint segment for restoring same to a normal or predetermined relationship with respect to one another following the application of torsional forces to the joint. While this prior art device may operate satisfactorily for the purposes intended, there is no provision for limiting the degree of rotation of the foot during walking and for applying a restoring torque to the foot for returning it to its initial position.

SUMMARY OF THE INVENTION

The invention includes a rotational joint assembly for a prosthetic leg which aids in controlling the retarding and restoring forces which are applied to an artificial foot as it is rotated during walking, running or turning. The prosthetic leg includes an upper member adapted to be connected to the wearer's body. This upper member may be connected to an artificial knee or through any suitable connector to a natural knee joint. The prosthetic leg also includes a lower member which is connected to an artificial foot. The rotational joint assembly is interposed between the upper and lower members of the prosthetic leg and includes a restrainer mechanism for applying a controlled force to limit the degree of rotation of the foot during walking and for applying a restoring force to return the foot back to its initial position. The restraining mechanism includes a resilient device which is carried by one of the upper and lower members, and a contact means which is carried by the other member so that as the foot is rotated during walking, the contact means bears against the resilient device deforming such. The degree of rotation of the foot is controlled by the deformation of the elastomer bearing. In one particular embodiment, the resilient device takes the form of a pair of spaced semicircular members having a space provided therebetween. The contact means includes a paddle element which is positioned between the semicircular members so that as such is rotated it will engage one or the other of the semicircular members. The surface of the semicircular member which engages the paddle element may be curved so as to regulate the amount of force applied to and through the paddle element.

Accordingly, it is an important object of the present invention to provide a rotational joint assembly for a prosthetic leg which may be interposed between an artificial knee or a natural knee and an artificial foot so as to enable the foot to be rotated slightly when walking, running or turning.

Another important object of the present invention is to provide a simple and efficient joint assembly for prosthetic legs which gives a controlled rotational movement to the foot for producing a more natural-like gait while walking and for minimizing the energy required in walking.

Still another important object of the present invention is to provide a joint assembly which controls the retarding and restoring forces of an artificial foot as such is rotated approximately plus or minus three degrees during walking.

Still another important object of the present invention is to allow the installation of rotational joints in standard 30mm tubing commonly used in lower limb prostheses.

These and other object and advantages of the invention will become apparent upon reference to the following specification, attendant claims, and drawing.

BRIEF DESCRIPTION OF THE DRAWING

FIG. 1 is a perspective view illustrating a prosthetic leg with the rotational joint assembly constructed in accordance with the present invention, FIG. 2 is an enlarged, sectional view illustrating the rotational joint assembly constructed in accordance with the present invention, FIG. 3 is an enlarged sectional view illustrating a modified form of the rotational joint assembly constructed in accordance with the present invention, and FIG. 4 is a sectional view taken along the line 4—4 of FIGS. 2 and 3.

DESCRIPTION OF THE PREFERRED EMBODIMENT

Referring in more detail to FIG. 1 of the drawing, there is illustrated a rotational joint assembly 10 constructed in accordance with the present invention as used with a conventional prosthetic leg 12. As illustrated, the prosthetic leg 12 is cut into sections 14 and 16 at a point located approximately, for example, eight inches from an artificial foot 18. Although the stump socket is indicated as being arranged for a below the knee amputation, it is to be understood that the pivot joint may be used with above the knee amputations as well. As illustrated, the sections 14 and 16 are tubular extensions extending from the rotational joint assembly 10 to the stump socket and to the artificial foot.

Referring to FIG. 2, the rotational joint assembly 10 includes an upper tubular member 20 which may be the lower end of a standard 30mm aluminum tubing that is utilized in prosthetic devices. A similar lower member 22 is connected to the artificial foot 18. The tubular members 20 and 22 can be the lower ends of tubular sections 14 and 16 or they can be inserted therein.

A metal or plastic connector 24 is inserted in the lower end of the upper tubular member 20 and secured thereto by welding or screws (not shown). The connector 24 provides a seat for receiving an elongated bolt 26. The bolt 26 is keyed to the connector 24 by a key 28 so as to insure that the bolt 26 does not rotate relative to the tubular member 20. A nut 30 is provided on an upper threaded end of the bolt 26 for securing such to the connector 24. The bolt 26 extends into the lower tubular member 22 and the connection therebetween will be discussed more fully below.

Interposed between the lower tubular member 22 and the upper tubular member 20 is a thrust bearing 31 which sits on top of a bearing support 32 that is, in turn, supported on the upper end of the lower tubular member 22. Such is to enable the lower tubular member 22 to rotate slightly relative to the upper tubular member 20.

The rotational joint assembly 10 further includes a restrainer mechanism for restraining or restricting the rotation of the lower tubular member 22. Positioned within the tubular member 22 is another circular tubular member 34. Carried within the tubular member 34 is a resilient device consisting of a pair of spaced semicircular elastomeric torque members 36 and 38 which are secured to the inner wall of the tubular member 34 by any suitable means such as adhesive. The inner surface of each of the semicircular elastomeric members 36 and 38 is arcuate with the greatest thickness being at the center of the tubular member 34 such as best illustrated in FIG. 4.

To restrain rotation of the lower tubular member 22, outwardly extending flanges 40 and 42 are welded to the shaft 26 to define a paddle element which is positioned between the two elastomeric torque members 36 and 38. These flanges 40 and 42 engage the elastomeric members 36 and 38 as the upper tube 20 is rotated relative to the lower tube 22 thereby limiting the rotation therebetween to a predetermined number of degrees for the unit torque applied. The retarding force applied by the resilient device to the paddle element is controlled by the curvature of the inner walls of the elastomeric members 36 and 38. The resiliency of elastomeric members 36 and 38 depends on the material from which they are made, as well as their length. The elastomeric members 36 and 38 are deformed by the flanges 40 and 42 engaging them and thereby causes a restricting of the rotational movement between upper and lower tubular members 20 and 22. then the rotational force is removed therefrom, a restoring torque is applied by the deformed elastomeric members 36 and 38, forcing the flanges 40 and 42 of the paddle element to return the tubular members 20 and 22 back to their initial position and, consequently, the artificial foot to its initial position. The contour of the inner surface of the elastomeric members 36 and 38 is such that as the angular rotation of the paddle element increases, the force required to rotate the paddle element further increases. It is to be understood that the restrainer mechanism may be constructed in such a manner that the resilient device has only one elastomeric member and the paddle element only one flange.

A thrust bearing 44 is carried on the shaft 26 in contact with a bearing set 46 that in turn is pressed against the lower end of the circular housing 34. A spring 48 is interposed between the bearing 44 and a washer 50 so as to apply a preload compression between the upper member 20 and the lower member 22 for preventing looseness that could generate noise and to allow the joint to act like a column in compression with no bending moment on the paddle shaft when side loads are applied. A nut 52 is carried on a threaded lower end of the shaft 26 and it can be rotated for varying the compression. FIG. 3 illustrates a modified form of the invention wherein instead of using the trust bearing 31, a low friction plastic swivel joint 54 is interposed between the upper tubular member 20 and the lower tubular member 22. An elastomeric compression bearing 56 is carried on the shaft 26 on the bottom side of the plastic swivel joint 54 and a washer 58 and nut 60 are provided for securing the assembly together. The shaft 26 extends through the tubular member 34 and has a washer 62 provided on the lower end thereof and a snap ring 64 for securing the shaft in place against a hard rubber or metal disk shaped member 66 which is pressed against the lower end of the tubular member 34. Therefore, the nut 60 can be adjusted for varying the compression load between the upper member 20 and the lower member 22. In one particular embodiment, the low friction plastic swivel joint 54 is constructed of Delrin with Teflon dispersed therein. The embodiment illustrated in FIG. 3 operates in the identical manner as the embodiment of FIG. 2 with the above mentioned exception. As previously mentioned, the restraining force applied by the elastomeric members 36 and 38 may be varied by changing either the material from which the elastomer is manufactured or the length of the elastomeric material or by varying the curvature of the inner walls.

In one particular embodiment, the elastomeric torque members 36 and 38 are constructed of silicone rubber. However, it is to be understood that they may be constructed of any suitable material, such as, natural rubber.

In operation, the rotational joint assembly can be installed in any suitable manner in a prosthetic leg normally between a knee joint and a foot. The knee joint may be either an artificial knee or may be a natural knee with a stump thereon to which a socket engages. The tubular members 20 and 22 may be the normal extensions from the stump socket and the artificial foot.

It has been found that in walking there is a normal rotation of the foot of approximately plus or minus 3 degrees. However, in artificial limbs, it has been difficult to reproduce this rotational movement and, as a result, the shoe on the artificial foot tends to be scuffed or dragged along the surface increasing the forces necessary to walk. Accordingly, as the user walks with the rotational joint installed, the foot will rotate approximately 3 degrees causing the flanges 40 and 42 of the paddle element to deform the elastomeric members 36 and 38. As the elastomeric members 36 and 38 are being deformed, they impart a retarding force to the rotation of the paddle element thereby limiting the rotation of a foot to approximately 3 degrees while walking. However, the more active the wearer of the prosthetic leg becomes, the greater the need for larger rotational angles and greater force transmission. As the rotation increases, the force required to rotate the foot further also increases due to the curvature of the elastomeric members. After the foot has been rotated when the leg is swung forward, then the elastomeric member imparts a restoring torque to the paddle element to return the foot to its initial position.

Both of the flanges 40 and 42 of the paddle element will bear against the surfaces of the elastomeric members 36 and 38 when the paddle element is in its neutral position.

However, when the patient is turning to the right or the left, such will in turn cause each flange on the paddle element to bear against only one of the surfaces of the elastomeric members depending upon which way the patient is turning.

While a preferred embodiment of the invention has been described using specific terms, such description is for illustrative purposes only, and it is to be understood that changes and variations may be made without departing from the spirit or scope of the following claims.

What is claimed is:

1. A rotational joint assembly for a prosthetic leg which applies retarding and restoring forces to an artificial foot as it rotated during the walking, running and turning of a wearer of said prosthetic leg, said joint assembly comprising:
   A. an upper member adapted to be connected to the wearer's body;
   B. a lower member adapted to be connected to said artificial foot;
   C. bearing means connecting said upper and lower members and permitting relative rotation therebetween;
   D. a resilient means carried by one of said members;
   E. a shaft carried by said other member; and
   F. an outwardly extending flange carried by said shaft for engaging said resilient means;
   G. whereby as said foot is rotated during walking, said flange bears against said resilient means for restricting the degree of rotation of said foot and for restoring said foot to its normal position.

2. The rotational joint assembly as set forth in claim 1 further comprising:
   A. a tubular housing carried by one of said members;
   B. said resilient means including a pair of spaced dimetrically opposed semicircular elastomeric members secured to an inner wall of said tubular housing; and
   C. said outwardly extending flange carried by said shaft positioned between said spaced diametrically opposed semicircular elastomeric members so that said flange engages said semicircular elastomeric members when said artificial foot is rotated.

3. A rotational joint assembly for a prosthetic leg which aids in controlling the retarding and restoring forces applied to an artificial foot as it is rotated during the walking, running and turning of a wearer of said prosthetic leg, said rotational joint assembly comprising:
   a. an upper tubular member;
   b. means for attaching said upper tubular member to the wearer's body;
   c. a lower tubular member adapted to be connected to said artificial foot;
   d. bearing means interposed between said upper and lower tubular members;
   e. a resilient means secured to an inner wall of said lower tubular member;
   f. a shaft carried by and extending downwardly from said upper tubular member into said lower tubular member;
   g. an outwardly extending flange carried by said shaft for engaging said resilient means as said upper tubular member is rotated relative to said lower tubular member;
   h. whereby rotation of said foot is retarded by said flange engaging and deforming said resilient means and said deformed resilient means forcing said flange and said foot back to their initial position.

* * * * *